United States Patent
Metz-Stavenhagen et al.

[19]

[11] Patent Number: 6,074,391
[45] Date of Patent: Jun. 13, 2000

[54] RECEIVING PART FOR A RETAINING COMPONENT OF A VERTEBRAL COLUMN IMPLANT

[75] Inventors: Peter Metz-Stavenhagen, Bad Wildungen; Bernd Robioneck, Preetz, both of Germany

[73] Assignee: Howmedica GmbH, Germany

[21] Appl. No.: 09/094,972

[22] Filed: Jun. 15, 1998

[30] Foreign Application Priority Data

Jun. 16, 1997 [DE] Germany ............... 297 10 484 U

[51] Int. Cl.[7] ........................................ A61B 17/56
[52] U.S. Cl. ........................... 606/61; 606/72; 606/73
[58] Field of Search ................... 606/61, 73, 72

[56] References Cited

U.S. PATENT DOCUMENTS

| | | | |
|---|---|---|---|
| 5,443,467 | 8/1995 | Biedermann et al. | 606/73 |
| 5,476,464 | 12/1995 | Metz-Stavenhagen et al. | 606/61 |
| 5,669,911 | 9/1997 | Errico et al. | 606/61 |
| 5,879,350 | 3/1999 | Sherman et al. | 606/61 |

FOREIGN PATENT DOCUMENTS

| | | |
|---|---|---|
| 348 272 A1 | 12/1989 | France . |
| 92 02 745 U | 4/1992 | Germany . |
| 195 07 141 A1 | 9/1996 | Germany . |

Primary Examiner—Michael Buiz
Assistant Examiner—Julian W. Woo
Attorney, Agent, or Firm—Lerner, David, Littenberg, Krumholz & Mentlik, LLP

[57] ABSTRACT

A receiving part for a retaining component of a vertebral column implant, having a fork-shaped section for receiving the retaining component, with the inner wall of the fork-shaped section including inner threaded portions into which there may be screwed a screw which, either directly or via a pressing element, acts on the retaining component in the fork-shaped section. The inner threaded portions and the outer thread of the screw comprises a saw tooth thread of a shape that the steep flanks of the inner threaded portions face away from the opening of the fork-shaped section.

28 Claims, 3 Drawing Sheets

RECEIVING PART FOR A RETAINING COMPONENT OF A VERTEBRAL COLUMN IMPLANT

BACKGROUND OF THE INVENTION

1. Field of the Invention

The invention relates to a receiving part for a retaining component of a vertebral column implant.

2. Description of Prior Art

With vertebral column implants there exists often the object of supporting certain vertebra of the vertebral column, of creating a tension between the vertebra or a compression in order to retain or change a relative position. For this purpose, suitable means are connected to the vertebrae which are subsequently described as retaining components and may be connected to one another by connecting means. As retaining components, there may be e.g. so-called pedicle screws which are screwed into the pedicle of the vertebrae. The head of the pedicle screw is either annular or fork-shaped. With annular pedicle screw heads e.g. a distraction rod is guided through and is fixed on both sides of the head with the help of a nut. With fork-shaped heads, it is known in the inside to provide threaded sections for a set screw with which a previously inserted distraction rod or likewise may be fastened.

A similar receiving part for a distraction rod or likewise is also known for hook-like retaining components, for example with so-called lamina hooks or pedicle hooks which are hooked into the corresponding vertebrae parts.

With fork-shaped receiving parts, there is the danger that on exerting a suitable pressing force on the distraction rod or likewise the arms of the fork-shaped part are bent apart by which means the fixation is compromised or even eliminated. It is known, for example, to counteract this in that a lifting eye bolt or nut is screwed on the outside around the receiving part in order to prevent the arms from bending apart. A so-called cap bolt has a similar effect, this bolt overlaps the receiving part at the open end and includes a centrally located peg-like section projecting into the recess of the fork-like part for fixation e.g. of a distraction rod.

From U.S. Pat. No. 4,946,458, it is also known to equip the end, on the head side, of a shank of a pedicle screw with a spherical bearing surface which is fastened in a corresponding bearing section of the head. By way of this, the shank of the pedicle screw may assume any angle with respect to the screw head. It has, however, been shown that it causes problems in securely fixing the relative position of the pedicle screw on the one hand and the receiving part or the head on the other hand.

SUMMARY OF THE INVENTION

It is the object of the invention to provide a receiving part for a retaining component of a vertebral column implant with which the retaining component may be securely fixed without the fork-shaped section being deformed.

With the receiving part according to the invention which may be the slotted head of a pedicle screw or a section of a lamina or pedicle hook, inner threaded sections are formed as a saw tooth thread. The steep flank of the saw tooth thread of the receiving part faces away form the opening of the fork-shaped section. It is to be understood that the thread of the set screw is complementary, i.e., the steep shank is aligned oppositely. Such a design of the thread causes essentially only a tension force on the arm sections of the fork-shaped section when the screw is pressed against the retaining component to be fastened. A bending apart of the tongs or arms does not occur.

By saw tooth thread, it is meant the tooth shape of FIG. 1 in which the flanks facing the opening at the top of FIG. 1 are angled at about 30° with respect to the horizontal and the flanks facing the bottom of FIG. 1 are steep and, as shown, generally horizontal.

The thread within the receiving part may be spaced from the free end. In this way, it is achieved that the set screw cannot be screwed in skewed. Also, the set screw at one end may have a smooth section in order to simplify the introduction of the screw particularly into the smooth initial section in the receiving part.

An advantage of the receiving part according to the invention also lies in the fact that it may be dimensioned smaller, since the bending forces on the fork-shaped head on account of the fastening of the retaining component with the help of a set screw largely do not occur.

As has been previously mentioned, the invention may be applied everywhere where, in a fork-shaped section, retaining components of vertebral column implants are to be fastened. The retaining component may according to one embodiment of the invention be a rod-like element, preferably a distraction rod. The retaining component may, however, also be formed by the shank of the pedicle screw, whose end near to the head is accommodated in a fork-shaped section. So that such a pedicle screw permits an angular position between the screw shank and the head. One embodiment of the invention provides that the end of the shank near to the head, which is broadened in diameter, comprises a spherical bearing surface which cooperates with a spherical bearing surface in the fork-shaped head. The end surface of the shank is convex, and between the screw and the inner surface there is arranged a disk which on the side facing the convex end surface may be plane or concave. Preferably, the curvatures of the end surface of the screw shank and of the facing side of the disk are formed with an approximately equal radius. On the opposite side, the disk according to a further embodiment of the invention may be planar. A set screw which cooperates with the fork-shaped head via a saw tooth thread then presses onto the disk which for its part fastens the shank of he pedicle screw at any angular position. It has been shown that such a design in the head region of the pedicle screw has the result of higher retaining forces so that the once assumed relative position of the shank to the head remains fixed even with larger forces. It is to be understood that between the set screw and the disk a distraction rod or likewise may be inserted through which the pressing force is transmitted to the disk, wherein the pedicle screw shank is fastened in the head of the pedicle screw assembly.

The disk may comprise an outer thread and be screwed into the head of the pedicle screw, wherein of course, the inner sides of the recess must be provided with a threaded section. Below this threaded section, there may be present a non-threaded section allowing free rotation which is reached when the disk is completely screwed in, bearing on the crowned surface of the end of the screw shank on the head side.

The disk may be provided on the periphery with radial slots so that a better bearing on the spherical end of the pedicle screw is made possible. The disk may further be provided centrally with an opening. Via the opening, a tool may engage with the facing end of the head of the shank of the pedicle screw and turn the shank. Moreover, the opening may be so dimensioned together with the concave surface of the disk, that a rod accommodated by the receiving part bears against the end, near to the head, of the pedicle screw shank when it is pressed with the set screw in the receiving part.

With the conventional pedicle screws, it is necessary that the fork-shaped head is pushed over the shank before the shank is rotated in. The handling of such a unit is, however, complicated. For this reason, one embodiment of the invention provides for the fork-shaped head to laterally comprise a slot, which is dimensioned such that the broadened end of the pedicle screw can be laterally introduced into the receiving space of the head. In this manner, the shank alone may be screwed into a vertebrae. The fork-shaped head may subsequently laterally be put onto the end of the pedicle screw shank which is near the head. Although the slot weakens the corresponding arm region of the head, but since the saw tooth thread is used, as has been cited several times, this prevents a bending apart of the head section, and the weakening is tolerable.

Another embodiment of the invention provides that on the outer side of the arms of the fork-shaped head diametrical recesses are formed. The recesses serve for accommodating a fork-shaped section which is part of a rotating or tensioning tool. With the help of the tool which can be applied in the recesses, the pedicle screw may be rotated. The tool may also laterally grasp the head so that a simultaneous access from above is still possible. It is to be understood that the recesses may be advantageous also with pedicle screws with a one-piece, formed-on head.

In order to securely fix a pedicle screw relative to the receiving part at any angle, one embodiment of the invention provides that the receiving part or head accommodates an annular cage. The cage comprises several slots which are formed by the lower side parallel to the axis. Furthermore, the inside the cage has a spherical concave bearing surface which cooperates with a convex end of the shank of the pedicle screw. The outer side of the cage has a conical surface which cooperates with a complementary conical surface in the receiving part. If a force is exerted on the cage in the direction of the pedicle screw, the cage is pressed radially together and by way of this exerts a pressing force onto the spherical surface of the screw shank. This pressure is sufficient to obtain a secure fastening of the screw shank relative to the receiving part.

BRIEF DESCRIPTION OF THE DRAWINGS

The invention is described in more detail by way of the drawings.

DETAILED DESCRIPTION OF THE INVENTION

Figure 1:
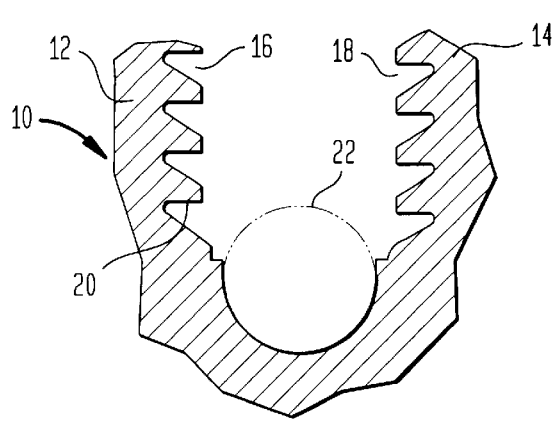
FIG. 1 shows a receiving part according to the invention, in section.

In FIG. 1, there is represented a receiving part 10 which is fork-shaped with arm sections 12, 14. The receiving part 10 may be the head of a pedicle screw or a section of a hook for a vertebral column implant. As can be recognized on the inner side of the arm sections 12, 14, there are formed threaded sections 16, 18 with a saw tooth shape. It is essential that the steep flank 20 of the saw tooth thread faces away from the open side of the receiving part 10. From the open side toward the corresponding recess of the receiving part 10, a distraction rod may be placed in as is shown dashed at 22.

Figure 2:
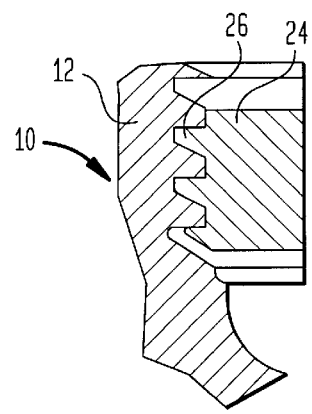
FIG. 2 shows a part of the receiving part according FIG. 1 together with a screw.

In FIG. 2, only the arm section 12 of the receiving part 10 is to be recognized. Further, a set screw 24 is to be seen which for its part comprises a saw tooth thread 26 which cooperates with the threaded sections 16, 18. The distraction rod 2 may be fixed in the receiving part 10 with the help of the set screw 24. Due to the shape of the thread on the arm sections 12, 14 with an axial force on the sect screw 24 essentially a tensional loading is exerted so that by way of this it is prevented that the arm sections 12, 14 are bent apart.

Figure 3:
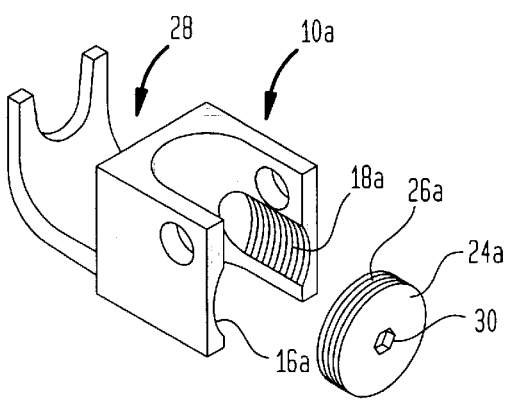
FIG. 3 perspectively shows a pedicle hook with a receiving part according to the invention.
Figure 4:
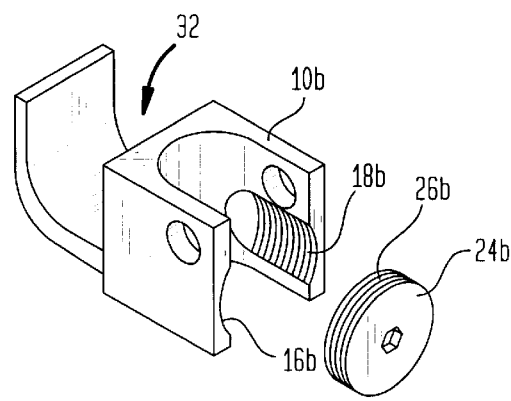
FIG. 4 show perspectively a lamina hook with a receiving part according to the invention.

FIG. 3 shows a pedicle hook 28 with a fork-shaped receiving part 10a which comprises threaded sections 16a, 18a in the shape of a saw tooth thread. A set screw 24a with a hexagon socket 30 comprises a corresponding saw tooth thread 26a.

A lamina hook 32 comprises a receiving part 10b with inner threaded sections 16b, 18b for receiving a set screw 24b with a saw tooth thread 26b. In both cases, in the receiving parts of the hooks 28 or 32, a distraction rod may be fixed.

Figure 5:
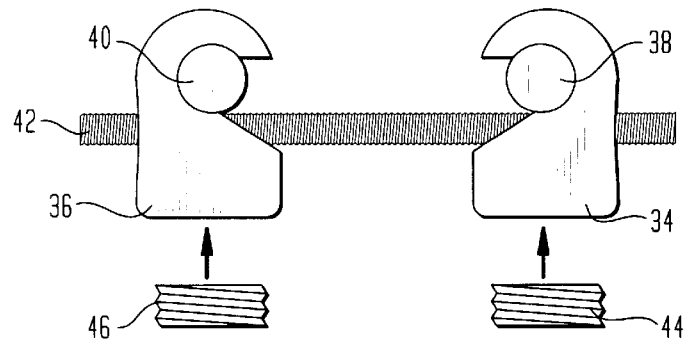
FIG. 5 shows the arrangement of two hooks for forming a bridge with a receiving part according to the invention.

In FIG. 5, there are shown two hooks 34, 36 which receive rod-like elements 38, 40. In the receiving parts of the hooks 34, 36, there is accommodated a distraction rod 42 which is channeled or provided with a thread and which bears against the rods 38, 40. With the help of set screws 44 or 46, the device shown, which forms a type of bridge, may be fixed. The set screws 44, 46 or the receiving parts of the hooks 34, 36 are in turn provided with a saw tooth thread of the above-mentioned type and manner.

Figure 6:
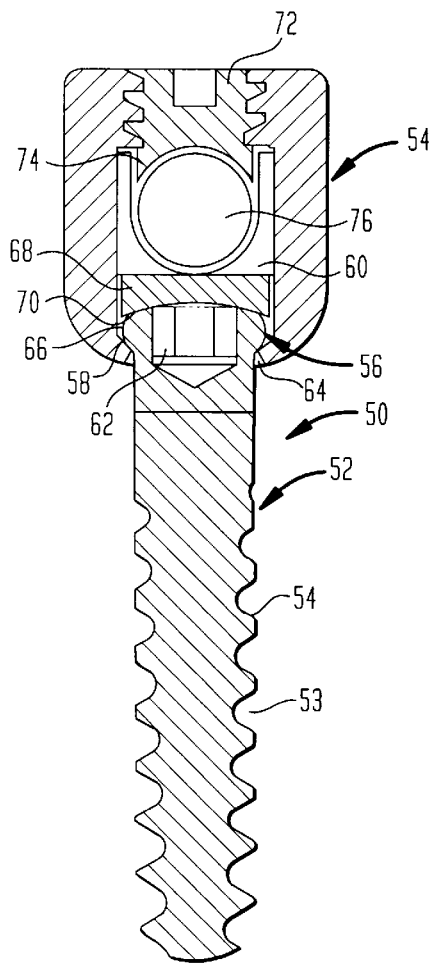
FIG. 6 shows a two-part pedicle screw with a receiving part according to the invention, in section.

In FIG. 6, there is represented a pedicle screw 50 with a shank 52 and a head 54. The shank 52 comprises a normal thread 54. The shank 52, is, at the end near to the head, formed with a broadened section 56 which on the lower side comprises an annular spherical bearing surface 58. Furthermore, the end surface of the broadened section is shaped spherically convex, as is shown at 60. The broadening has a hexagon socket 62 for receiving a corresponding rotational tool.

The head 54 is fork-shaped similar to the receiving part 10 and at the end facing the shank 52 is provided with an opening 64 through which the shank 52 extends. A part of the wall of the opening 64 comprises an annular spherical bearing surface 66 which cooperates with the spherical bearing surface 58. The shank 52 may therefore assume in a limited spacial angle, any angular position to the head 54.

In the receiving space of the head 54, there is arranged a disk 68 which on the upper side is planar but on the lower side comprises a concavely curved surface with a curvature which corresponds to the end surface 60 of the shank 52. The disk 68 is inserted approximately fittingly into the inner space of the end 54 so that it is radially secured as shown in FIG. 6. The disk 68 may be provided with an outer thread, and the inner thread of the head 54 may extend until shortly above the opening 64, 66. In this way, the disk 68 may be screwed in until it reaches free rotation and here by way of a corresponding contact pressure can be pressed into engagement with the crowned end of the shank 52. The outer thread of the disk 68 and the inner threaded sections in the inside of the head 54 are not provided with reference numerals.

Referring to FIG. 6, a set screw 72 is threaded into inner threaded sections of the head 54, wherein the threaded sections again comprise a saw tooth thread. A shank 74 of the screw 72 cooperates with the planar surface of the disk 68 and presses this against the end surface 60 of the shank 52. In this manner, the angular position between the head 54 and the shank 52 can be effectively fixed.

At 76 there is shown in phantom a distraction rod via which a pressure may be exerted onto the disk 68, wherein the rod for its part may be fixed in its position. It is to be understood that the shank 74 of the screw 72 must be designed correspondingly shorter. It is still to be mentioned that the shank 74 at the lower end is convexly rounded.

Figure 7:
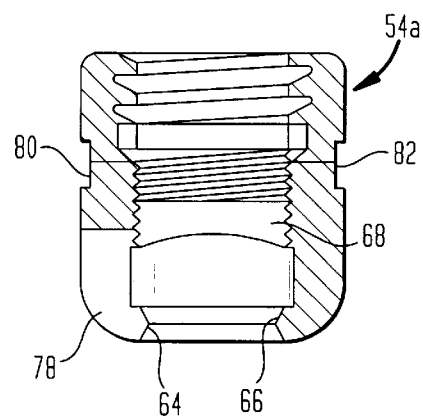
FIG. 7 shows a receiving part similar to that according to claim 6, but with additional features.

In FIG. 7, the head of a pedicle screw similar to that according to FIG. 6, is shown. It, however, has some modifications. Thus, the head is indicated as 54a. One recognizes that the head 54a laterally in the region near the shank comprises a slot 78, via which the end, near the head, of the shank 52 may be inserted. Thus, the shank 52 firstly can be screwed into a pedicle of a vertebrae after which subsequently the head 54a is placed on.

On the outer side of the arm sections of the head 54a, there are formed slots 80, 82 for receiving the prongs of a hook-like tool section which laterally grasps the head on the outside in order to exert a tension effect or to rotate the head. It is to be understood that the slots 80, 82 may also be mounted on a head formed as one piece with the shank.

Figure 8:
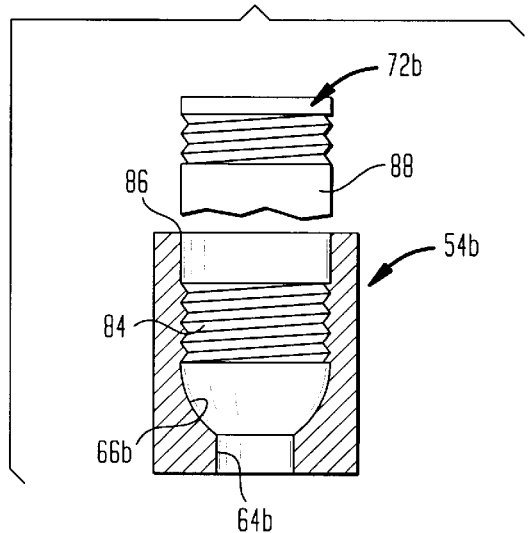
FIG. 8 schematically shows a possible modification of the receiving part according to FIG. 6.

The embodiment form according to FIG. 8 differs from the receiving part or the head 54 according FIGS. 6 or 7 in that in the inside near to the free end there is provided a thread-free section 86 to which connects a threaded section 84. The screw 72b comprises at one end likewise a thread-free section 88. The outer diameter of the thread-free section 88 corresponds approximately to the inner diameter of the thread-free section 86. In this way, the screw 72b may be inserted straight into the head 54b and subsequently screwed.

Figure 9:
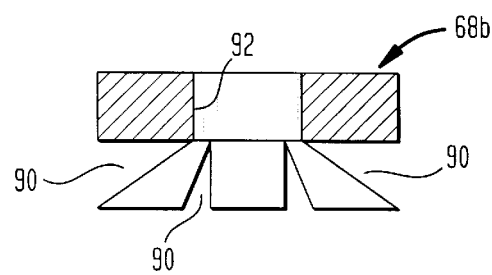
FIG. 9 show s schematically a disk modified with respect to FIG. 6.
Figure 10:
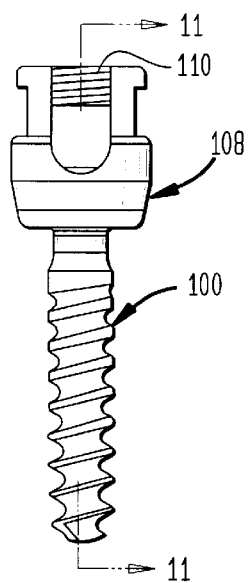
FIG. 10 shows a pedicle screw with a modified receiving part.

The disk 68b according to FIG. 9 differs from the disk 68 according to FIG. 6 in that proceeding from the periphery a row of radial slots 90 s formed which are spaced in the circumferential direction. The slots permit an effective bearing of the disk 68b on the spherical convex surface 60 of the screw shank 52 according to FIG. 6. Moreover, the disk 68b comprises a passage opening 92. This permits the guiding through of a tool for engagement into the recess 62 of the screw shank 52 according to FIG. 6.

In the FIGS. 10 to 14, there is shown a further embodiment of the invention. The pedicle screw represented in FIGS. 10 and 11 comprises a screw shank 100 which is formed roughly as the screw shank 52 according to FIG. 6. At the upper end, the shank 100 comprises a spherical section 102 which from the free end is provided with a recess 104 for a rotational tool As can be recognized in FIG. 11, the section 102 is accommodated by a cage 106 which can be more clearly recognized in FIGS. 13 and 14. The cage is seated in a receiving part 108 which in the upper region comprises oppositely lying recesses and is thus fork-shaped, as can be recognized in FIG. 10.

The receiving part 108 which forms the head for the pedicle screw is provided with diametrically opposite threaded sections 110 which are formed corresponding to the threaded sections 16 according to FIGS. 1 and 2. In the part lying thereunder, the receiving part 108 is formed in the manner of an annular housing 112 which on the inner side comprises a conical annular surface 114 which converges downwardly. Via a lower opening 116, the cage 106 which is represented in the FIGS. 13 and 14, may be introduced.

Diametrically opposite on the outer side of the head 108, recesses 188 are formed for receiving a tool, not shown, for screwing in the pedicle screw.

Figure 11:
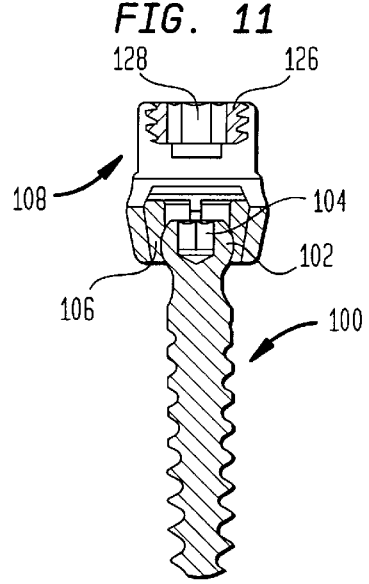
FIG. 11 shows a section through the representation according to FIG. 10 taken along the line 11—11.
Figure 12:
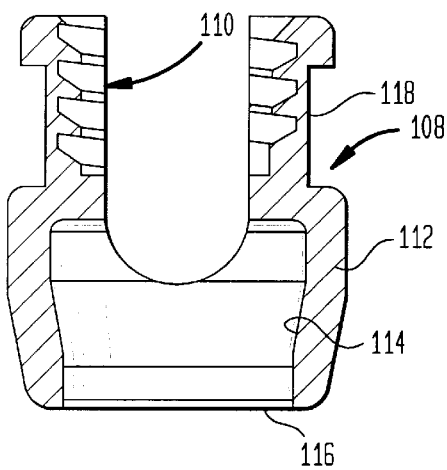
FIG. 12 shows in a larger scale the receiving part of the embodiment form according to FIGS. 10 and 11.
Figure 13:
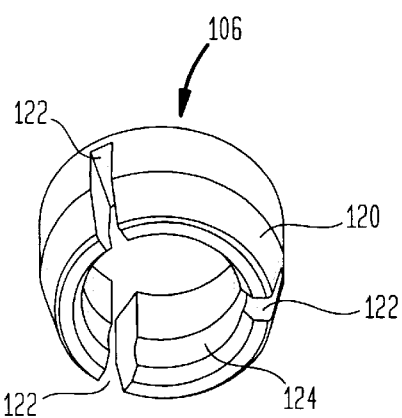
FIG. 13 shows perspectively the cage of the embodiment form according to FIGS. 10 and 11.
Figure 14:
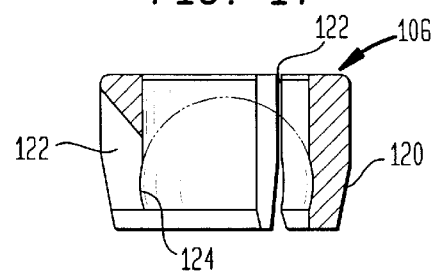
FIG. 14 shows a section through the cage according to FIG. 13.

The annular cage 106 comprises on the outer side a conical annular surface 120 which cooperates with the conical surface 114 of the receiving part 108 as can be recognized in FIG. 11. The cage 106 is furthermore provided with three slots 122 parallel to the axis, wherein one of the slots is continuous so that the annular cage 106 is parted or split in the circumferential direction. On the inner side, the cage 106 comprises a spherical bearing surface 124 which accommodates the spherical section 102 of the shank 100, as is shown in FIG. 11.

Into the threaded sections 110, there is screwed a screw 126 (FIG. 11) which centrally comprises a continuous hole 128 for leading through a tool with which the shank 100 can be rotated. With the help of the screw 126, there is fastened a distraction rod which is now shown and which is accommodated by the fork-shaped section of the head 108. The rod is pressed against the cage 106. Bay way of this, the cage 106 is moved downwards in the direction of the screw shank 100 and is radially pressed together. In this manner, the spherical section 102 is clamped in the cage 106 and the angular position between the shank 100 and the head or the receiving part may be fixed.

What is claimed is:

1. A receiving part for a retaining component of a vertebral column implant comprising a fork-shaped section for receiving the retaining component having an opening at a first end, an inner wall of the forked-shaped section is formed with an inner threaded into which a set screw may be threaded from said opening to act directly on indirectly on the retaining component in the fork-shaped section, said inner thread of the fork-shaped section and an outer thread of the set screw comprise a thread of a shape having generally horizontal flanks which on the inner thread face away from the opening of the fork-shaped section and mating flanks of the set screw face towards the opening.

2. The receiving part according to claim 1, wherein the fork-shaped section is a slotted head of a pedicle screw.

3. The receiving part according to claim 1, wherein the fork-shaped section is formed by a shank of a hook.

4. The receiving part according to claim 1, wherein the retaining component is a rod-like element.

5. The receiving part according to claim 1, wherein the retaining component is the shank of a pedicle screw having a first end near to the retaining component accommodated in the fork-shaped section.

6. The receiving part according to claim 5, wherein an end of the shank has an enlarged diameter and comprises a spherical bearing surface which cooperates with a spherical counter bearing surface in the fork-shaped section, said end surface of the shank is convex and a disk is located between the set screw and the end surface.

7. The receiving part according to claim 6, wherein the disk is slidingly accommodated by the fork-shaped head.

8. The receiving part according to claim 6, wherein the side of the disk facing the set screw is planar.

9. The receiving part according to claim 6, wherein the side of the disk facing the pedicle screw is concave.

10. The receiving part according to claim 6, wherein the disk is generally circular in cross section and includes several radial slots spaced around a circumferential direction and extend inwardly from a periphery of the circumference of said disk.

11. The receiving part according to claim 9, wherein the disk comprises a central opening.

12. The receiving part according to claim 11, wherein the concave surface of the disk and the central opening are dimensioned such that a rod accommodated by the receiving part bears against a spherical surface of an end of the pedicle screw which is near the head.

13. The receiving part according to claim 6, wherein the disk comprises an outer thread and said fork-shaped section comprises inner threaded portions with which the outer thread of the disk engages, wherein the thread in said fork-shaped section adjacent said first end of the shank is terminated to allow for the free rotation of the disk.

14. The receiving part according to claim 6, wherein the fork-shaped head laterally comprises a slot which is dimensioned such that the enlarged end of the shank may be laterally introduced into a receiving space of the receiving part.

15. The receiving part according to claim 2, wherein on an outer side of the fork-shaped head diametrical recesses are formed for receiving a fork-shaped tool.

16. The receiving part according to claim 5, wherein the shank of the pedicle screw at the upper end comprises a spherical section, an annular cage is provided which comprises several slots parallel to an axis of said cage which are spaced in the circumferential direction and which are open towards a lower end, and which on the inside of said cage is a spherical bearing surface and the cage on an outer side comprises a conical surface which cooperates with a conical inner surface of the receiving part in a manner such that on pressing the cage into the receiving part in the direction of the shank the cage is compressed radially.

17. The receiving part according to claim 16, wherein the cage is parted by a radial continuous slot.

18. A receiving part for a pedicle screw comprising:
a head section at a first end of the receiving part defining a receiving space and an aperture for receiving a shank of the pedicle screw at a second end and a slot adjacent said second end extending laterally from said aperture, said slot having an open end to allow the shank of the pedicle screw to be laterally introduced into the aperture.

19. The receiving part as set forth in claim 18, wherein said head section is generally U-shaped.

20. The receiving part as set forth in claim 19, wherein said U-shaped section includes an inner surface having threads formed about a longitudinal axis of said receiving part.

21. The receiving part as set forth in claim 18, wherein said aperture is for receiving an enlarged portion of said pedicle screw shank, said aperture being smaller in cross-section than said enlarged portion of said shank.

22. The receiving part as set forth in claim 21, wherein an inner surface of said receiving part includes threads and said part further includes a set screw engageable with said threads.

23. A receiving part as set forth in claim 18, wherein said head section includes internal threads having steep flanks said steep flanks of said inner threads of said head section are generally horizontal and said inner threads further including inclined flanks facing towards said first end.

24. A method for assembling a pedicle screw, having an enlarged portion at the end of a threaded shank, into a retaining part comprising:
providing a retaining part having a fork-shaped section at a first end thereof and an aperture for receiving the shank of the pedicle screw at a second end thereof and a slot extending laterally from said aperture and having an open end;
moving the enlarged portion of the pedicle screw and said shank in a direction transverse to a longitudinal axis thereof into and through said lateral slot and into said aperture.

25. A receiving part for receiving a pedicle screw having an enlarged portion at the end of a threaded shank, comprising:
a head portion at a first end including a first bore extending along an axis of said receiving part;
an aperture communicating with said first bore formed at a second end of the receiving part for receiving the shank of the pedicle screw; and
a second bore extending along an axis transverse to said axis of said first bore communicating with said first bore and said aperture.

26. The receiving part as set forth in claim 25, wherein said aperture is part circular and centered along the axis of the first bore.

27. The receiving part as set forth in claim 26, wherein a cross-section of said aperture is smaller than a cross-section of said enlarged head.

28. The receiving part as set forth in claim 1, wherein said steep flanks of said inner threads of said head section are generally horizontal and said inner threads further including inclined flanks facing towards said opening.

* * * * *

UNITED STATES PATENT AND TRADEMARK OFFICE
CERTIFICATE OF CORRECTION

PATENT NO. : 6,074,391
DATED : June 13, 2000
INVENTOR(S) : Metz-Stavenhagen et al.

It is certified that error appears in the above-identified patent and that said Letters Patent is hereby corrected as shown below:

Column 6, line 50, "threaded" should read -- thread --.
Column 8, line 3 "s et" should read -- set --.

Signed and Sealed this

Tenth Day of April, 2001

*Attest:*

NICHOLAS P. GODICI

*Attesting Officer*     *Acting Director of the United States Patent and Trademark Office*

UNITED STATES PATENT AND TRADEMARK OFFICE
CERTIFICATE OF CORRECTION

PATENT NO.    : 6,074,391
DATED         : June 13, 2000
INVENTOR(S)   : Metz-Stavenhagen et al.

It is certified that error appears in the above-identified patent and that said Letters Patent is hereby corrected as shown below:

Column 6,
Line 51, "on" (first occurrence) should read -- or --.

Signed and Sealed this

Fifteenth Day of July, 2003

JAMES E. ROGAN
*Director of the United States Patent and Trademark Office*